US 8,078,667 B2

(12) United States Patent
Pohjanen (10) Patent No.: US 8,078,667 B2
(45) Date of Patent: Dec. 13, 2011

(54) METHOD AND SYSTEM FOR DATA TRANSFER, AUXILIARY SERVER AND EXAMINATION DEVICE

(75) Inventor: Petri Pohjanen, Oulu (FI)

(73) Assignee: Optomed Oy, Oulu (FI)

( * ) Notice: Subject to any disclaimer, the term of this patent is extended or adjusted under 35 U.S.C. 154(b) by 0 days.

(21) Appl. No.: 12/523,218

(22) PCT Filed: Jan. 15, 2008
(Under 37 CFR 1.47)

(86) PCT No.: PCT/FI2008/050008
§ 371 (c)(1),
(2), (4) Date: May 21, 2010

(87) PCT Pub. No.: WO2008/087250
PCT Pub. Date: Jul. 24, 2008

(65) Prior Publication Data
US 2010/0293219 A1 Nov. 18, 2010

(30) Foreign Application Priority Data
Jan. 17, 2007 (FI) .................................... 20075025

(51) Int. Cl.
G06F 15/16 (2006.01)
(52) U.S. Cl. ......... 709/202; 709/203; 709/217; 709/219
(58) Field of Classification Search .................... None
See application file for complete search history.

(56) References Cited

U.S. PATENT DOCUMENTS

| | | | | |
|---|---|---|---|---|
| 6,304,788 B1 * | 10/2001 | Eady et al. | ...................... | 700/86 |
| 6,757,719 B1 | 6/2004 | Lightman et al. | | |
| 6,760,755 B1 * | 7/2004 | Brackett | ........................ | 709/214 |
| 7,430,608 B2 * | 9/2008 | Noonan et al. | ................ | 709/230 |
| 7,840,694 B2 * | 11/2010 | Yamaki | .......................... | 709/232 |
| 2003/0072424 A1 * | 4/2003 | Evans et al. | ............... | 379/106.02 |
| 2003/0105389 A1 | 6/2003 | Noonan et al. | | |
| 2004/0019464 A1 | 1/2004 | Martucci et al. | | |
| 2005/0086328 A1 * | 4/2005 | Landram et al. | .............. | 709/220 |
| 2005/0209889 A1 | 9/2005 | Funahashi | | |
| 2006/0012678 A1 | 1/2006 | Broas | | |
| 2006/0246921 A1 | 11/2006 | Russ | | |
| 2007/0118635 A1 | 5/2007 | Nakano | | |
| 2007/0244997 A1 * | 10/2007 | Tindal | ........................... | 709/220 |
| 2011/0054343 A1 * | 3/2011 | Chetham et al. | .............. | 600/547 |

FOREIGN PATENT DOCUMENTS

| | | |
|---|---|---|
| FI | 107120 B | 6/2001 |
| FI | 1114198 B | 9/2004 |
| JP | A-2005-165648 | 6/2005 |
| KR | B1-10-0691513 | 3/2007 |
| WO | WO 2004/070995 A2 | 8/2004 |
| WO | WO 2006/106965 A1 | 10/2006 |

* cited by examiner

*Primary Examiner* — John B. Walsh
(74) *Attorney, Agent, or Firm* — Oliff & Berridge, PLC (57) ABSTRACT

A system for data transfer comprises a server of a patient data system and an auxiliary server, which has installation data associated with at least one accepted device identifier available. The auxiliary server receives the identifier determining an examination device and transmits the installation data associated with the examination device identifier to the server of the patient data system. The server of the patient data system installs the identifier determining the examination device automatically on the basis of the installation data on the server of the patient data system for data transfer. Data is transferred between the examination device and the server of the patient data system after the identifier has been installed.

29 Claims, 5 Drawing Sheets

METHOD AND SYSTEM FOR DATA TRANSFER, AUXILIARY SERVER AND EXAMINATION DEVICE

FIELD

The invention relates to a method and a system for data transfer, an auxiliary server and an examination device for data transfer.

BACKGROUND

To examine organs, such as eyes, ears or skin, digital optical auxiliary instruments may be used as help. For instance, by using a portable camera unit suitable for opthalmoscopy, otoscopy and dermatoscopy, a digital image in electrical form may be produced from the pictured object. Since the camera unit may be connected by a cable to a computer, still picture(s) or video may be transferred to the computer for image processing, analysis and presentation.

Different institutions, such as hospitals and health centres, usually have a patient data system including a centralized server for storing and retrieving patient data. However, data produced by a portable camera unit cannot be directly stored in the server of the patient data system. Therefore, the storage in the server, if it is even attempted, requires several different steps and that data is input separately and manually. In addition, patient data from the patient data system is either not available at all or can only be seen poorly on the computer screen after complex operations or is printed on paper in connection with an examination carried out with the portable camera unit.

BRIEF DESCRIPTION

It is an object of the invention to implement an improved method and a system implementing the method, an auxiliary server and an examination device for data transfer.

This is achieved by a method for data transfer, the method comprising using an examination device for producing electrical data from an organ. The method comprises receiving an identifier determining the examination device by an auxiliary server, which has installation data associated with at least one accepted device identifier available; transmitting the installation data associated with the examination device identifier from the auxiliary server to a server of a patient data system; automatically installing the identifier determining the examination device on the basis of the installation data on the server of the patient data system for data transfer; and transferring data between the examination device and the server of the patient data system after installing the identifier.

The invention also relates to a system for data transfer, the system comprising an examination device for producing electrical data from an organ. The system comprises an auxiliary server, which has installation data associated with at least one accepted device identifier available; the auxiliary server being arranged to receive an identifier determining the examination device and transmit the installation data associated with the examination device identifier from the auxiliary server to a server of a patient data system for an automatic installation; and the examination device being arranged to transfer data with the server of the patient data system after the identifier has been installed.

The invention also relates to an auxiliary server. The auxiliary server has installation data associated with at least one accepted device identifier available; the auxiliary server is arranged to receive an identifier determining an examination device and transmit the installation data associated with the examination device identifier to a server of a patient data system for an automatic installation to allow data transfer between the examination device and the server of the patient data system after the identifier has been installed.

The invention also relates to an examination device for producing electrical data from an organ. The examination device is arranged to transmit its identifier to an auxiliary server to transmit installation data associated with the identifier to a server of a patient data system for an automatic installation; and the examination device is arranged to transfer data with the server of the patient data system after the identifier has been installed.

Preferred embodiments of the invention are described in the dependent claims.

The method, system, auxiliary server and examination device of the invention provide a plurality of advantages. Data transfer becomes simpler and data processing during examination is easy. In addition, the examination device may be easily connected to patient data systems of various institutions, such as hospitals.

LIST OF FIGURES

The invention will now be described in greater detail in connection with preferred embodiments with reference to the attached drawings, in which.

DESCRIPTION OF THE EMBODIMENTS

An examination device, which comprises a hand-held camera unit, may automatically communicate either wirelessly or via a fixed connection with systems of the environment by using a compatible communication protocol and storage mode to store and process digital information produced with the camera unit in these systems. The processing, if required, may be carried out in its entirety in the device or together with the system of the environment or entirely in the system of the environment.

The camera unit of the examination device may be very much similar to the solutions described in Finnish Patents FI 107120 and FI 20021233, wherefore all features of the camera unit known per se are not explained in this application in greater detail, but the focus is on the features of the described solution differing from the prior art.

Figure 1:
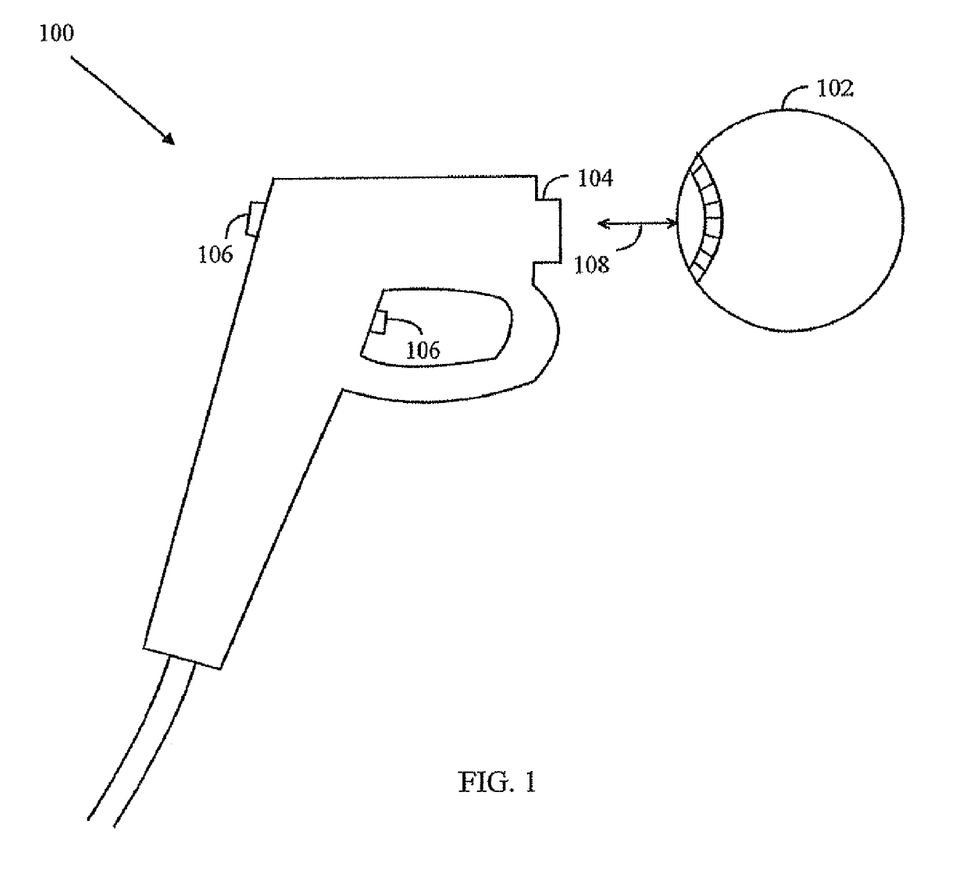
FIG. 1 illustrates an eye examination carried out with a camera unit.

Let us first examine the solution according to the presented solution by means of FIG. 1, in which the organ to be examined is an eye 102. In this example, the examination device is a camera unit acting as a detection unit 100, which may be a portable, hand-held digital camera, the appearance of which possibly resembles that of a pistol to some extent. The camera unit acting as a detection unit 100 may comprise a lens or lenses for producing an image, an optical radiation source for illuminating the object from which an image is captured, and a user interface 106 for switching on and off and using the device and/or inputting data. The camera unit acting as a detection unit 100 may also comprise a processor and memory for controlling the device and processing and storing information, and a display for displaying an image and other feasible data. The detecting component of the camera unit may be a CCD (Charge Coupled Device) cell or a CMOS (Complementary Metal Oxide Semiconductor) cell, and the camera unit may produce still pictures or video image.

According to the presented solution, from an end piece 104 of the camera unit acting as a detection unit 100, which is suitable for eye examination, optical radiation 108 proceeds to the eye 102 to be examined and, reflected from the eye 102, back to the camera unit. The presented solution is not only restricted to eye examination, but the solution may be employed similarly to examine mouth, throat, nose, ear and skin. Therefore, different type of end pieces suitable for imaging purposes and objects may be attached to the camera unit.

In addition to or instead of a camera unit, the detection unit 100 may also comprise, for instance, a stethoscope, an ultrasonic transceiver, a sensor wristband, a combination of the previous devices, or a similar device measuring the state of one or more organs.

Figure 2:
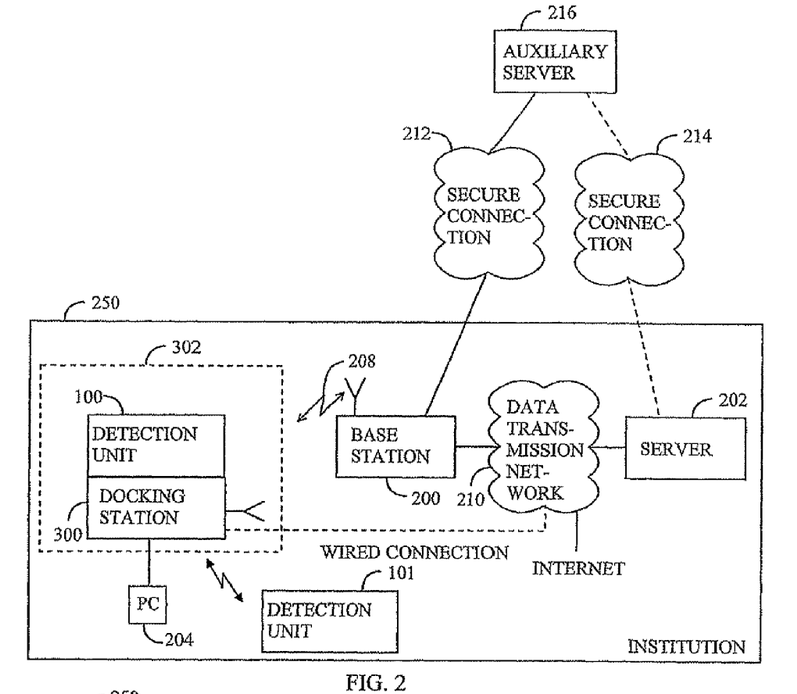
FIG. 2 illustrates data transfer between a camera unit and a server of a patient data system, when an auxiliary server is located outside a local network.
Figure 3:
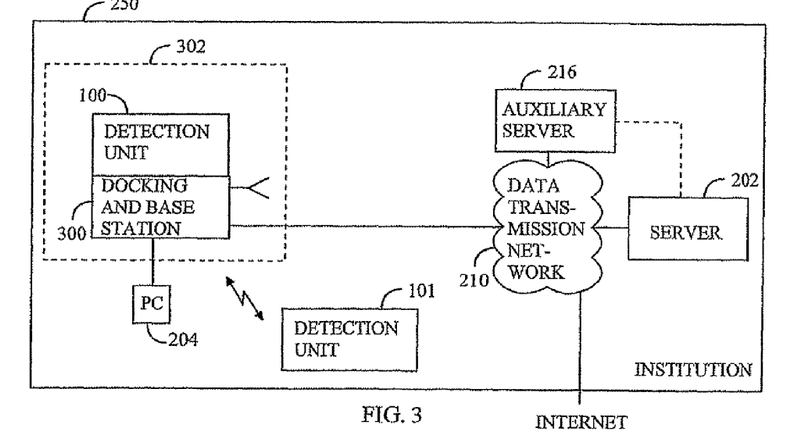
FIG. 3 illustrates data transfer between a camera unit and a server of a patient data system, when an auxiliary server is located inside a local network.

Let us now examine by means of FIGS. 2 and 3 possibilities to implement data transfer between the camera unit acting as a detection unit 100 and a server 202 of a patient data system. An examination device 302 may be an entity formed by the camera unit acting as a detection unit 100 and a docking station 300. A server block 202 of the patient data system may also comprise an auxiliary server 216 and a centralized server, even though they may also be physically separate units.

In FIG. 2, a base station 200 of a hospital (or other institution) and the docking station 300 are shown as independent units. The detection unit 100 may include means for providing a wireless connection with the docking station 300, or the detection unit 100 and the docking unit 300 may perform data transfer only via a wired connection or a direct contact. Alternatively or in addition, the detection unit 100 may comprise means for providing a direct wireless connection with the base station 200.

When the camera unit acting as a detection unit 100 is switched on, the camera unit may automatically establish a connection with the base station 200 or the user manually controls the camera unit acting as a detection unit 100 to establish a connection with the base station 200. Alternatively or in addition, the camera unit may establish a connection with the docking station 300, which may perform the probably necessary data processing, because data transfer does not always succeed by using a direct connection to the base station 200. The docking station 300, in turn, may establish a connection or be already in connection with the base station 200, whereby a connection is formed between the detection unit 100 and the base station 200. The base station 200, for its part, may have, e.g. via a data transmission network 210, a wired connection with the server 202, which is the internal server of the patient data system of a hospital or other similar institution 250. The base station 200 may then act as an access point between the wireless and wired systems. The camera unit acting as a detection unit 100, the docking station 300 and the base station 200 may transmit and receive radio-frequency electromagnetic radiation. This may be implemented by using, for instance, RF (Radio Frequency) parts, the activity of which is based on, for example, WLAN (Wireless Local Area Network), Bluetooth® and/or mobile telephone technology, such as GSM (Global System for Mobile communication) or WCDMA (Wide-band Code Division Multiple Access). When a Bluetooth® solution is employed, the range covers dozens of metres, the range of a WLAN solution is hundreds of metres and with mobile telephone technology, the range may even be dozens of kilometres.

The base station 200 and the docking station 300 may also be combined as one device, as shown in FIG. 3, in which case it can be thought that the docking station 300 also comprises base station functions. Thus, a separate base station 200 is not needed. The examination device 302 may thus be in a wired connection with the data transmission network 210 and act as a base station for other devices, which are in connection or try to establish a connection with the server 202.

When the detection unit 100 is connected to the docking station 300 by means of a USB (Universal Serial Bus) connector, for example, information may be transferred from the detection unit 100 to the docking station 300, from which the information may be transmitted in real time or after a desired delay to the base station 200 and further to the server 202. Correspondingly, information may be transferred from the server 202 to the base station 200, which transmits the information to the docking station 300 and further to the detection unit 100. The docking station 300 may also be in connection with the computer 204, the connection to which may be implemented by using, for example, a USB interface or a LAN (Local Area Network).

Another camera unit or other examination device 101 may communicate through the examination device 302 with the server 202 in such a manner that the examination device 302 may be responsible for the communication via the base station 200 and/or the network to the server 202. The examination device 302 may thus act as a transmitter of the produced data between other devices of the system, which do not communicate wirelessly with the systems of the environment, and the environment.

Instead of a wireless connection, the docking station 300 may also be in a wired connection with the data transmission network 210. The detection unit 100 may also be in connection with the computer 204, such as a PC (Personal Computer). The connection to the computer 204 may be implemented by using a USB interface, for example.

When the examination device 302 is connected to the data transmission network 208, 210 of the patient data system, the examination device 302 may transmit its identifier to the auxiliary server 216. The identifier may be transmitted to the auxiliary server 216 in secured form via a secure connection 208, 210, 212, for example. The identifier may be a device identification, which may have, for example, a textual form and may comprise the device name and model, for instance.

The examination device 302 may transmit its identifier wirelessly to the base station 200 of the data transmission network 208, 210 of the patient data system, which base station may transmit the identifier of the examination device 302 to the auxiliary server 216. The identifier may be transmitted to the auxiliary server 216 in secured form via the secure connection 208, 210, 212, for example.

The base station 200 may transmit the identifier of the examination device 302 to the auxiliary server 216 via the data transmission network 208, 210 of the patient data system.

The detection unit 100 representing the examination device 302 may transmit the identifier to the docking station 300, which transmits to the auxiliary server 216 at least one of the following: a detection unit 100 identifier, a docking station 300 identifier. The identifier may be transmitted to the auxiliary server 216 in secured form via the secure connection 208, 210, 212, for example.

The detection unit 100 identifier and/or the docking station 300 identifier may be transmitted from the docking station 300 to the auxiliary server 216 via the data transmission network 208, 210 of the patient data system.

When the examination device 302 comprising the detection unit 100 and the docking station 300 is connected to the data transmission network 208, 210 of the patient data system, the docking station 300 identifier may be transmitted from the docking station 300 to the auxiliary server 216, the identifier also determining the detection unit 100. The identifier may be transmitted to the auxiliary server 216 in secured form via the secure connection 208, 210, 212, for example.

The auxiliary server 216 may receive the identifier determining the examination device 302 via the secure connection 208, 210, 212. The identifier may be received via the secure connection 208, 210, 212, for example.

The auxiliary server 216 has installation data associated with at least one accepted device identifier available. The auxiliary server 216 may be a hospital's server, in which information on the acquired device required when the device purchased is stored and updated. The information may be input manually and retrieved automatically from the manufacturer's server, for instance. The auxiliary server 216 may also be a server maintained by the manufacturer, from which information on each device can be retrieved, for instance, via the Internet.

The auxiliary server 216 may transmit the installation data associated with the examination device 302 identifier to the server 202 of the patient data system. The transmission may be carried out via the secure connection 208, 210, 212, 214.

The secure connection 208, 210, 212, 214 may be the hospital's own internal and secure data transmission network or a data transmission network which extends at least partly outside the hospital and in which data to be transferred may be secured by an encryption program. One of such connection forms is SSH (Secure SHell), which may be used when logging in to the server.

The identifier determining the examination device 302 may be installed automatically on the basis of the installation data on the server 202 of the patient data system for data transfer. After the identifier has been installed, data transfer may be started between the examination device 302 and the server 202 of the patient data system. Correspondingly, the identifier of any other device may be installed on the server 202 in a similar manner and the data transfer may be started.

This method thus aims to authenticate either the detection unit 100, the docking station 300 or the entire examination device 302. If the authentication of the examination device 302 is not successful, the server 202 reports the problem. The nature of the problem may also be reported. For instance, it may deal with a wrong form of fields in the data format or incompatibility of the data format and the server 202. The docking station 300 or the base station 200 may process the data into a form suitable for the server 202, whereby, for instance, the forming of the fields and the data format may be corrected. Alternatively, the docking station 300 may control the detection unit 100 to process the data to be suitable for the server 202.

Figure 4:
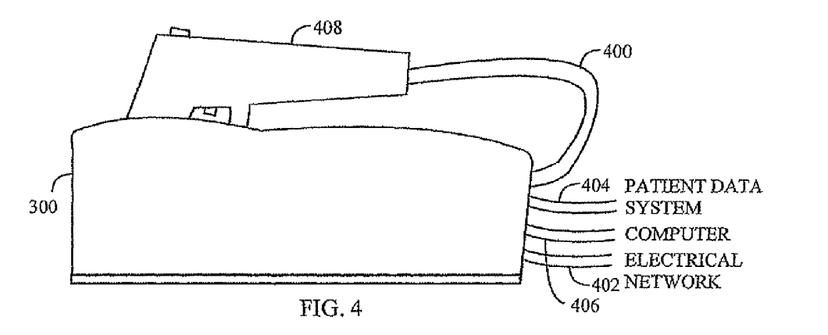
FIG. 4 shows a camera unit connected to a docking station.

FIG. 4 shows a camera unit 408 acting as a detection unit 100 and connected to the docking station 300. The docking station 300 may be connected by a conductor 402 to a public electrical power network, from which the docking station 300 takes electric power and may use it for its own operation and convert it to a form required by the camera unit 408. Between the camera unit 408 and the docking station 300 there is a cable 400, along which the docking station 300 supplies the camera unit 408 with the required electric power in order to charge the battery of the camera unit 408, for instance. The docking station 300 may also be shaped in such a manner that the camera unit 408 may be placed firmly in its place in the docking station 300 when the camera unit 408 is not used for examining an organ. Also the docking station 300 may comprise a battery. By means of a conductor 404, the docking station 300 may be connected to the data transmission network 210 of the patient data system in the network, or the docking station 300 may be in a wireless connection with the base station 200 acting as an access point during data transfer with the server 202. The docking station 300 may also be in connection with e.g. a PC via a cable 406.

Data transfer between the examination device 302 and the server 202 of the patient data system may be carried out partly or entirely by communicating in accordance with a DICOM (Digital Imaging and Communications in Medicine) protocol. It may deal with a wired or wireless data transfer. It is also possible to perform data transfer between some other examination device and the server 202 via the examination device 302. In this case, image data of the examination device 302, having e.g. a DICOM form, may be combined with data of another examination device or other device, which may be, in addition to or instead of image data, e.g. voice data. Voice data may be, for instance, heart beat sounds detected by a stethoscope acting as a detection unit 100, or a doctor's speech, a conversation between a doctor and a patient, etc. received by a detection unit.

The DICOM protocol is used like a standard in health care institutions, such as hospitals, health centres, different clinics, etc. Therefore, the server 202, which is often a database belonging to the data transmission network of the institution, is capable of communicating according to the wired DICOM protocol. Instead, the wireless communication between the base station 200 and the examination device 302 may be performed in accordance with the DICOM standard or something else. The protocol defines the compatibility between different systems when medical images are produced, stored, displayed, processed, transmitted, retrieved from the memory or printed. Thus, the DICOM standard not only determines the communication protocol but also the record protocol. The DICOM protocol is compatible with the HL7 (Health Level 7) standard, which also deals with using and processing clinical and administrative data on health care and which may be the form of communication connection that is used between the examination device 302 and the server 202. The DICOM protocol utilizes, for instance, the following standards: LOINC (Logical Observation Identifiers, Names and Codes), SNOMED (Systematized Nomenclature of Medicine), JPEG (Joint Photographic Experts Group), MPEG (Moving Picture Experts Group) and TCP/IP (Transmission Control Protocol/Internet Protocol).

A DICOM file comprises a heading, which includes besides the actual image data a field for determined data and a field for data in free format. One DICOM file may comprise one or more images. The DICOM protocol may be used for combining different data types, such as image data, video data, audio data and alphanumerical data into a data set belonging to the same connection. The stored data concerning one patient thus remains as associated data and is not mixed with data on other patients.

Figure 5:
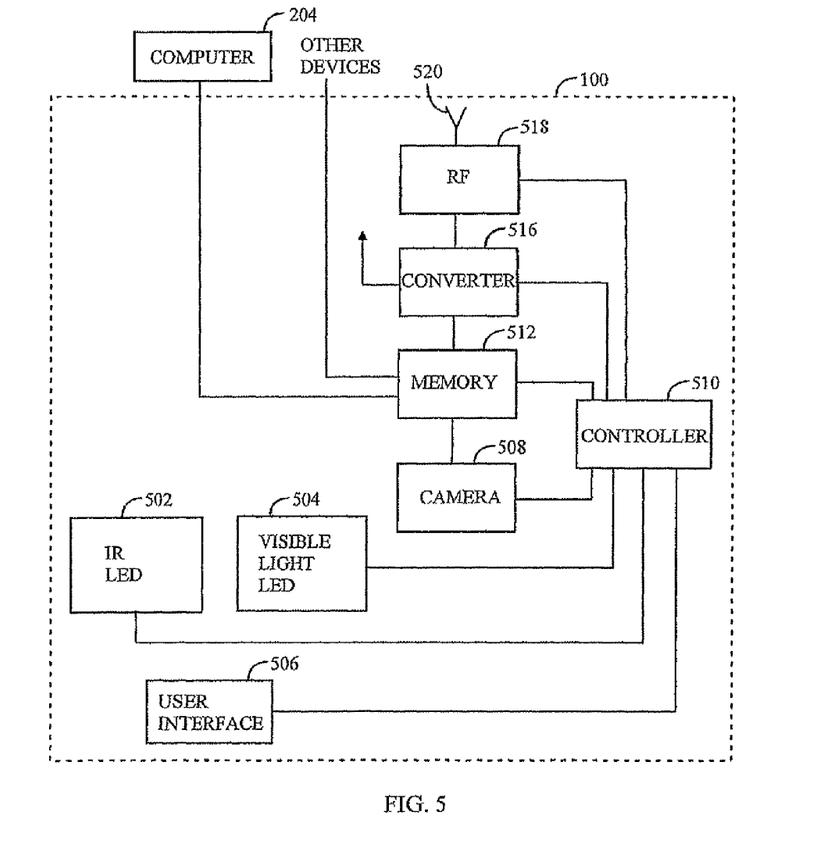
FIG. 5 shows a block diagram of the camera unit.

FIG. 5 shows a block diagram of the camera unit 408 acting as a detection unit 100. The camera unit 408 may comprise an infrared radiation source 502, a visible light source 504, a user interface 506, a camera 508, a controller 510 and a memory 512. The controller 510, which may comprise a processor, controls the operation of the camera unit 408. Image data may be transferred from the camera 508 to the memory 512, from which the image data may be transferred to the display of the user interface 506 and/or elsewhere, controlled by the controller 510. Still pictures or video image of the object from which an image is captured may be stored in the memory 512, which may be of a flash type and repeatedly detachable and attachable, such as a SD (Secure Digital) memory card.

The camera unit 408 may display a real-time video image or a last-produced still picture of the object from which an image is captured on the display. Image processing procedures facilitating the diagnosis, such as adjustment of colour saturation or illumination, may be performed immediately in connection with imaging. The processing may also be performed in the docking station 300 or the base station 200 either in real time or during data transfer.

When data is transferred from the camera unit 408 towards the server 202, the data may, if required, be converted according to a suitable standard in a converter 516. The camera unit 408 does not necessarily include a converter 516, but it may alternatively be located in the docking station 300 or the base station 200. The converter 516 may convert the data format used by the camera unit 408, which may be e.g. an XML format, to a data format according to the DICOM protocol, for instance. The converted data may then be transferred to RF means 518, where the data is mixed up to the radio frequency. The radio-frequency signal is transmitted via the antenna 520 as electromagnetic radiation, which may be received at the base station 200.

The antenna 520 may receive electromagnetic radiation containing data and transmitted by the base station 200. The signal propagates from the antenna 520 to the RF means 518, where the radio-frequency signal is mixed down to baseband data. The converter 516 may convert the data format of the received data to something else, if necessary. In this case, for example, the DICOM data format may be converted to a data format used by the camera unit 408. The converted data may be transferred to the memory 512 and, if needed, connected as desired to the picture taken by the camera 508 in a manner controlled by the controller 510. Text or a scale may be added to the picture taken, or different pictures may be set on top of one another. Also, auditory or acoustic data may be attached to the picture. Data may be transferred from the memory 512 to the display and a feasible loudspeaker, for example.

If the camera unit 408 uses a SDIO (Secure Digital Input Output) card, the radio connection be realized directly with a WLAN or Bluetooth® connection supported by the SDIO card. The SDK) card may also be used for a radio connection in the base station 200 and the docking station 300. The radio connection may also be implemented such that inside the camera unit 408 there is a USB connector, to which a USB-WLAN adapter is attached, or the printed circuit board of the camera unit 408 comprises a WLAN transceiver.

The converter 516 is not necessarily needed if the data format of data to be transferred from the camera unit 408 to the base station 200 or even to the server 202 remains the same.

The memory 512 is not necessarily needed if the pictures taken by the camera 508 are transferred directly over radio path to the base station 200. However, at least some kind of buffer memory is often required to secure the data transfer.

From the patient information, which may be the data retrieved from the server 202, a desired or necessary part may be shown on the display in the beginning of, during or after the examination. The patient list may be displayed by the camera unit 408 independently or controlled by the docking station 300. At first, before the patient has come into the room, a patient list may be transferred to the camera unit 408, from which the doctor may choose the patients to be examined in order. The rest of the patient data may include earlier diagnoses about the patient and other similar cases. The patient list may be transmitted with the DICOM message, and if the camera unit 408 does not support the DICOM protocol, the docking station 300 or the base station 200 may convert the message to a suitable form in such a manner that the patient list can be seen on the graphical user interface of the camera unit.

Patient information or other data attached to a picture, which may be data retrieved from the server 202, may be utilized in real time e.g. in such a manner that image data is automatically supplied to a desired object, such as a centralized server, from which doctors may, if desired, retrieve data to be consulted, or automatically to a specific doctor or group of doctors, which has committed to provide a real-time or almost real-time consultation e.g. through the network systems.

By means of wireless communication, the camera unit 408 is capable of automatically identifying the environment where it is located. When the camera unit 408 is switched on, it may be pre-configured to receive and transmit, for instance, radio signals or TCP/IP traffic, which are in accordance with the DICOM protocol. The camera unit 408 may thus identify its location in an institution by, for instance, identifying the identifier of the base station or base stations in its coverage area. The identification may be based on the IP address of the base station or other identification, for example. Other identification solutions may be WLAN positioning, RFID identification, in which a room, a docking station or a base station transmits an RFID identifier, identification by an identifier card (doctor or patient), identification by a wristband of a patient, etc. Data may be processed and transmitted to a desired server according to the location information.

Data may also be transferred from the examination device 302 to the computer 204, which may have an image-processing program. The computer may receive data from the examination device wirelessly throughout the entire examination. After the doctor has finished the examination, the computer may convert the data it has received to DICOM data, for example.

A still frame or a continuous video image produced by the camera and processed by the image-processing program may be displayed visually on the display of the computer 204. The user interface of the computer may comprise a keyboard and a mouse for controlling the computer and inputting data. Image processing procedures facilitating the diagnosis, such as adjustment of colour saturation or illumination, may be performed immediately in connection with imaging, and the imaging may be followed from the display of the computer 204 during the examination.

By using the computer 204, it is also possible to take a single image by means of image capturing. In this case, the still image that was captured may be displayed on the display of the computer. Image data may also be stored in the memory of the computer. The memory may be RAM (Random Access Memory) and ROM (Read Only Memory), a hard disk, a CD (Compact Disc) or similar memory means known per se.

Figure 6:
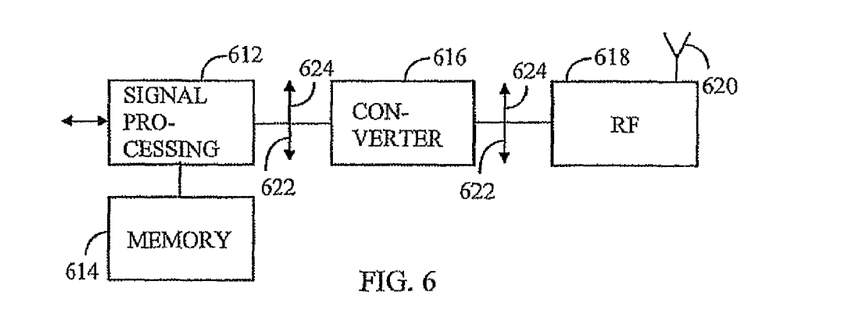
FIG. 6 shows a block diagram of the docking station.

FIG. 6 shows a block diagram of a docking station. When the purpose is to transfer data between the detection unit 100 and the docking station 300 like in FIGS. 2 and 3, the docking station 300 may comprise a signal processing unit 612, which comprises a processor and a necessary signal processing program, a memory 614, a converter 616, RF parts 618 and an antenna 620, which may correspond to the converter 516, RF means 518 and antenna 520 of the camera unit 408. Besides the RF connection, the docking station 300 may be provided with other wireless connection 622 and/or a connector 624 of a wired connection before or after the converter 616. The wireless connection may be implemented, for instance, with a WLAN radio, a WIMAX radio, a Bluetooth radio or a WUSB radio. The connector of the wired connection may be, for instance, a USB connector, a Firewire connector or a connector of a fixed network. In addition to or instead of connecting the docking station 300 to a general electrical network, it may comprise a chargeable battery (not shown in FIG. 6) as a power source.

The signal processing unit 612, which may also be responsible for controlling the operation of the docking station 300, is not necessarily required if the desired signal processing and the operation control are performed by the detection unit 100, the base station 200 or the server 202. The memory 614 is not necessarily required either.

The converter 616 of the docking station 300 may, however, be required in such a case, for instance, that the camera unit 408 does not have a converter 516 and the converter 516 is needed for converting the data format. By using the RF means 618 of the docking station, data may be mixed to a radio-frequency signal, which may be transmitted from the antenna 620 to the base station 200. Correspondingly, the antenna 520 of the docking station may receive a radio-frequency signal containing data from the base station 200. By using the RF parts 618, the received signal may be mixed down to data and, if required, its data format may be converted with the converter 616. Data may further be signalled to the camera unit 408 as data to be displayed to the user or data controlling the camera unit 408. The docking station 300 may also be in a fixed or wireless connection with the computer 204 and via the network with the server 202.

The operating system of the docking station 300 may be programmable because, for example, the features of the docking station 300 and thus the features of controllable devices may be improved. This may be necessary, if the docking station is responsible for image data processing, in which case a new type of image processing may also require a new type of programming in the interfaces of the devices.

The docking station 300 may search for examination devices 302 to be connected to the data transmission network 208, 210 of the patient data system and read the identifier of the detected examination device 302. The docking station 300 may transmit the identifier of the examination device 302 it has read to the auxiliary server 216. The transmission may take place via a secure connection 208, 210, 212.

By means of the detection unit 100 of the examination device 302 or the docking station 300, at least one wireless connection to the base station 200 may be implemented by using different techniques, such as WLAN, Bluetooth® or mobile telephone technology. In this case, the detection unit 100 or the docking station 300 may transmit a signal or tries to receive a signal by various possible ways. When the examination device 302 receives a proper signal from the base station 200 in at least one of the tested manners, the examination device 302 may use this at least one operating connection possibility when communicating with the base station 200. Similarly the base station 200 may search for a suitable way of connecting to the examination device 302.

The docking station 300 may control the operation of the camera unit 408 and the data transfer between the camera unit 408 (or other detection unit) and the server 202 of the patient data system, for example, in the following way if the detection unit supports that the docking station manages its operation. The same docking station 300 may control the operation and data transfer of different camera units 100 or other examination devices differently, because, for instance, different detection units 100 may be used for different examination purposes.

The docking station 300 may control the imaging process of the camera unit 408 and storage of the image data in the memory of the camera unit 408, the docking station 300, the computer 204 or the server 202. Generally, the docking station 300 may control the data storage of the detection unit 100 in different memories.

The docking station 300 may control image data processing during the imaging. The image may then be processed, analyzed and the image may be stored. The docking station 300 may, for example, convert data it has received from the camera unit to a DICOM form.

The docking station 300 may control the retrieval of patient data from the server 202 or the computer 204 and the data storage in the server 202 and the computer 204.

The docking station 300 may control the attaching of patient data to image data produced by the camera unit 408. Generally the docking station may control the attaching of patient data to data produced by the detection unit 100.

The docking station 300 may establish a TCP/IP connection with a wired or wireless system of the environment.

The docking station 300 or the base station 200 may establish a UPnP (Universal Plug and Play) connection or a medical UpnP connection with the environment and the devices supporting it.

The docking station 300 may manage the instructions of a graphical user interface and a feasible graphical user interface of the detection unit 100, such as the camera unit 408, according to the data obtained. In this case, the patient data may be displayed on the display of the examination device 302. The solution may be implemented, for instance, such that in the examination device 302 the graphical user interface is formed with by an XML (Extensible Markup Language) or HTML (HyperText Markup Language) description language, which may be processed in real time.

Let us now examine functional features of the examination device 302. Either the docking station 300 alone, the detection unit 100 alone or the docking station 300 and the detection unit 100 together perform the following procedures. The examination device 302 may, by a separate user prompt or automatically, detect the patient data system to be used and the examination device 302 may thus automatically communicate with the patient data system. Known devices intended for the examination of eye, ear or skin do not include any automatism for identifying or establishing a communication protocol with specific software or a specific system, but the devices only act as parts producing images or other data. They are not wireless or usable in any kind of operating environment so that data produced by them could automatically be added to the data systems of the organization, for instance. Similarly, the examination device 302 may identify a suitable alternative for a connection to the computer 204 or other devices and/or systems of the environment.

The examination device 302 may retrieve its own program, for instance, from the server of the Internet or other server, if no suitable software is included in the examination device 302 itself. The examination device 302 may also transmit a request for processing data by means of a program of the server 202. The server 202 may transmit an accepting acknowledgement concerning the request to the examination device 302, after which the examination device 302 may start the desired software by means of the server 202.

The examination device 302 may transmit the material it has produced, for instance, to a consultation system in the Internet and further control the existing software used e.g. in the computer to use this consultation system as one data transmission system.

The examination device 302 may receive certain standard data on patient appointments, such as appointment scheduling, transmitted by patient data systems. The examination device 302 may combine the information produced with the camera unit with this appointment scheduling and transmit the produced information on a certain patient to the server and/or the computer.

The examination device 302, i.e. the detection unit 100, or the docking station 300 may act as transmitting equipment for other devices, which aim to communicate with certain systems of the environment. Other device may be, for example, an ultrasonic device, which communicates with the examination device 302. The examination device 302 may thus further communicate with the server 202 operating in the network by possibly storing patient-specific image data and voice data.

The examination device 302 may identify the system of the environment and the programs with which the examination device 302 is programmed to operate. In addition, the examination device 302 may, automatically or in a controlled manner, communicate with the system of the environment. This makes it also possible to start the software of the computer 204 directly from the memory of the examination device 302 (autorun, CD ROM emulation) so that the user does not need to do any settings to put the device into operation with these programs. This may be implemented, for instance, in such a manner that the software is stored in the FLASH memory of the examination device 302, from which it may be taken into use automatically. The examination device 302 may also retrieve settings associated with at least one communication mode from the server 202, 216 for the communication to be established with at least one device of the environment.

The examination device 302 may search for and identify the operating system of the computer 204 and whether the computer contains desired patient data programs. If at least one desired patient data program is found, the examination device 302 may, in a controlled or automatic manner, start the patient data program and pick the desired information from there.

The detection unit 100 may, e.g. by a separate prompt or automatically, receive from the computer 204 or elsewhere from the environment parameters and communication protocol rules, by which the connection to the base station 200 and via the base station to the server 202 is possible.

The detection unit 100 may start its own software for storing and processing data from its own memory, if no known software for processing and commenting the produced data is available from the server 202 or the computer 204. In this case, e.g. the camera unit 408 may start a report form wirelessly, for instance, in the computer 202 in the vicinity, by means of which the image data produced by the camera unit may be stored in this computer 202 together with a textual sick report, for instance.

Correspondingly, the software that is started from the memory of the detection unit 100 may be such that it complements the sick report software used by the doctor and automatically found in the computer 202. Such a complementary property may be, for example, a capability of transmitting the material produced with the software in the computer 202 to a specific server 204 operating in the network, which can only be accessed by the user of the detection unit 100. The docking station 300 may also perform these functions.

The detection unit 100 may control the docking station 300 to communicate with the features of the environment to provide the best possible data storage method.

The examination device 302 may start the desired function or software (e.g. a "lite" version of the device's own memory or the network's server) of the computer 204 in such a manner that the user automatically obtains the image data produced with the device to his/her use.

At least a part of the fixed or exchangeable memory of the examination device 302 may be visible to the computer 204 as a mass memory, such as a USB memory.

The detection unit 100 or the docking station 300 may identify the used protocols and communicate by using them according to the settings obtained from the auxiliary server 216, for example. Thus, the camera unit or the docking station 300 may establish a MESH type wireless connection to the base station 200. In this case, each node only needs to transmit a signal to the closest node in order to transfer a signal from any node to any other node. Nodes, in turn, may include all devices belonging to the network, such as devices used by the users, e.g. the detection unit 100 or the docking station 300 and the base station 200.

The detection unit 100 or the docking station 300 may establish a GRID type connection to the base station 200. A GRID type connection may be established wirelessly between the camera unit and the base station in such a manner, for instance, that the connections are 'bundled', which means that, for instance, there are simultaneously three WLAN connections with three WLAN radios from the camera unit to the base station and two USB connections from the camera unit to the base station. The connection may also be established as a combination of a WLAN connection and a Bluetooth connection, for example. A fast radio connection is thus provided in such an environment that uses, for instance, an old WLAN network (of the class 802.11b) and a few base stations.

The detection unit 100 or the docking station 300 may also establish a P2P (Peer-To-Peer) type connection to the base station 200. In this protocol, all connection parties have the same chances to start the connection and participate in the data transfer. By using the P2P connection, the detection unit 100 may transmit data in small packets at a time when it is in connection via different networks, for example. If, for instance, the camera unit 408 is transported in coverage areas of different base stations or it is in the vicinity of a plurality of docking stations which all have a connection to the storage location, such as a local computer or a host computer, data from the camera unit 408 may be transmitted to said storage location or locations in packets. A P2P type connection may be used, for instance, if the room contains a plurality of examination devices 302, each of which is connected to the network, whereby the server, for instance, could be surely provided with a fast connection of uniform quality to the storage, even if the radio network would change at some point. The P2P connection also enables that information on one patient provided by different devices may be combined as one set of patient data. The patient data may be in accordance with the DICOM protocol.

When the docking station 300 is used, the docking station 300 may determine a connection to the detection unit 100. The determination concerns the communication mode, encryption, etc., and the determination may be carried out, even though the server 202 based on the DICOM protocol would determine, for example, the encryption for the traffic which may be in accordance with the TCP/IP protocol.

The docking station 300 may control the functions of the detection unit 100 in such a manner that, for instance, image transfer from the camera unit 408 and erasure of the camera unit's 408 memory are performed under control of the docking station 300 after each examination. This ensures that different patients' data are not mixed up with each other, for instance, so that there is still data on the previous patient in the detection unit 100 when a new patient is examined.

The docking station 300 may determine new features for the detection unit 100 so that the control of the feature's functionality is transferred to the detection unit 100 but the actual processing of the functionality remains under control of the docking station 300. For example, if a new printer is acquired in an institution or examination room, the docking station 300 may search for the new device in the environment and determine that the printing is carried out from the detection unit 100 connected to the docking station 300 to this printer exactly.

The produced data to be transferred and stored may be encrypted by the detection unit 100 and/or the docking station 300 to protect the patient data from outsiders. Image data may be stored on the basis of the patient data, whereby it is possible to limit the use of the image data to the patient in question. When medical data is added to the image, the use of the image may be restricted to a desired doctor or desired doctors.

The detection unit 100 or the docking station 300 may also automatically control the received and transmitted data communication according to a predefined priority and with a predefined encryption. Thus, the patient may only authorize himself and the nursing doctor, for example, to use the stored data. The information on the priority and feasible encryption may be obtained via a wireless connection, transmitted by the base station 200 from the server 202 or elsewhere from the patient data system. The key transmitting the encryption may also be transmitted to the examination device from the patient's identifier, such as a smart card. This may happen, for instance, so that when the patient registers in the hospital for an examination, he/she may order all patient data concerning him/her to be encrypted. The information on the encryption may at first be stored in the server and then transferred from the server to the examination device as a DICOM message, for instance. When the patient is examined with the examination device, the examination device may retrieve the encryption key, for instance, from the server in the Internet, which the patient has announced in connection with the encryption information.

The detection unit 100 or the docking station 300 may obtain a new update from the server 202, 216 or elsewhere from the patient data network, or the server 202, 216 or other part of the patient data system may control the detection unit 100 to operate efficiently with respect to the new feature. If, for example, a new printer is acquired in the institution or the examination room, the server 202 or some other part of the patient data system may determine the printing to be carried out from the detection unit 100 to this printer exactly. The detection unit 100 or the docking station 300 itself may also establish a connection in order to update functions in the server 216 or 202, which is responsible for maintenance.

The detection unit 100 or the docking station 300 may also receive data wirelessly from other examination devices, such as a stethoscope, sensor wristbands, etc. This information may be attached to the data provided by the detection unit 100.

Figure 7:
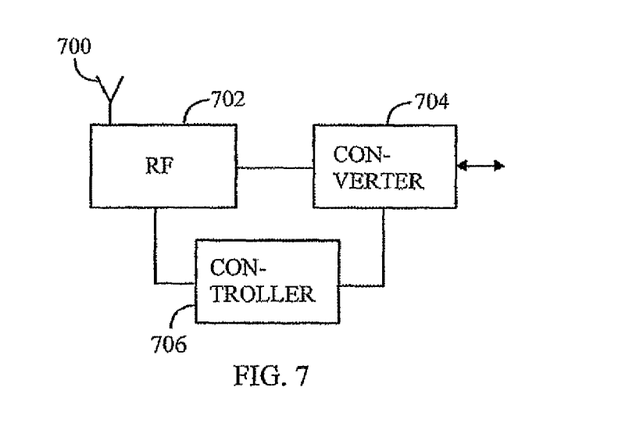
FIG. 7 shows a block diagram of a base station.

FIG. 7 shows a block diagram of a base station. The base station 200 receives radio-frequency electromagnetic radiation with an antenna 700. The received signal propagates to RF means 702, in which the radio-frequency signal is mixed as baseband data. The data format of the received data, for its part, may be converted in a converter 704, after which the data may proceed via the data transmission network to the server 202. Correspondingly, the data format of the data from the server 202 may be converted in the converter 704, from which the data proceeds to the RF means 702 to be mixed to a radio frequency. A radio-frequency signal, for its part, may be transmitted via the antenna 700 as electromagnetic radiation. The operation of the base station 200 may be controlled by a controller 706, which may comprise a processor, memory and a necessary computer program.

Figure 8:
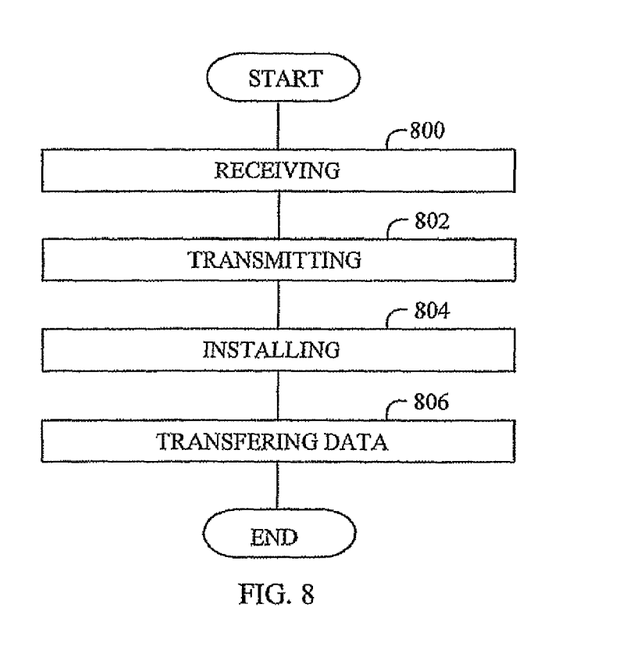
FIG. 8 shows a flow chart of a method.

FIG. 8 shows the flow chart of the method. In step 800, an identifier determining the examination device 302 is received by the auxiliary server 216, which has the installation data associated with at least one acceptable device identifier available. In step 802, the installation data associated with the identifier of the examination device 302 is transmitted from the auxiliary server 216 to the server 202 of the patient data system. In step 804, the identifier determining the examination device 302 is automatically installed on the basis of the installation data on the server 202 of the patient data system for data transfer. In step 806, data is transferred between the examination device 302 and the server 202 of the patient data system after the installation of the identifier.

The method illustrated in FIG. 8 may at least partly be implemented as a logic circuit solution or a computer program. A computer program may be located in a distribution means of the computer program for its distribution. The distribution means of the computer program is readable by a data-processing device and it encodes computer program commands to transfer data in connection with an interactive procedure.

The distribution means may be a solution known per se for distributing a computer program, such as a medium readable by a data-processing device, a program storage medium, a memory readable by a data-processing device, a software distribution package readable by a data-processing device, a signal readable by a data-processing device, a telecommunication signal readable by a data-processing device, and a compressed software package readable by a data-processing device.

Figure 9:
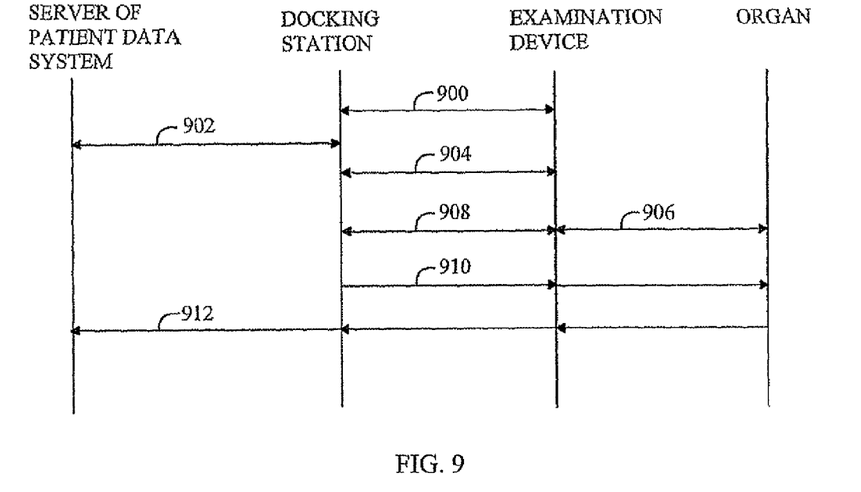
FIG. 9 shows a protocol diagram of the docking station.

FIG. 9 shows a protocol diagram, by which the docking station's signalling between different parts may be carried out. In step 900, the docking station finds the controllable devices of the environment automatically or in a controlled manner. In step 902, the base station, automatically or in a controlled manner, inquires the control and functionality values of the devices found in the environment from the server 216 or the computer 204. In step 904, the docking station is in a wired or wireless connection with the devices of the environment. In step 906, a picture of the patient is being taken with a device intended for examining the fundus of the eye, for example. In step 908, the docking station communicates with the examination device about the functionality associated with the processing of the imaging event. In step 910, the docking station performs the processing of the imaging and controlling of the imaging. In this case, instructions may be displayed, for instance, on the display of the examination device. In step 912, the base station transfers the obtained image data to the computer or the server 202.

Figure 10:
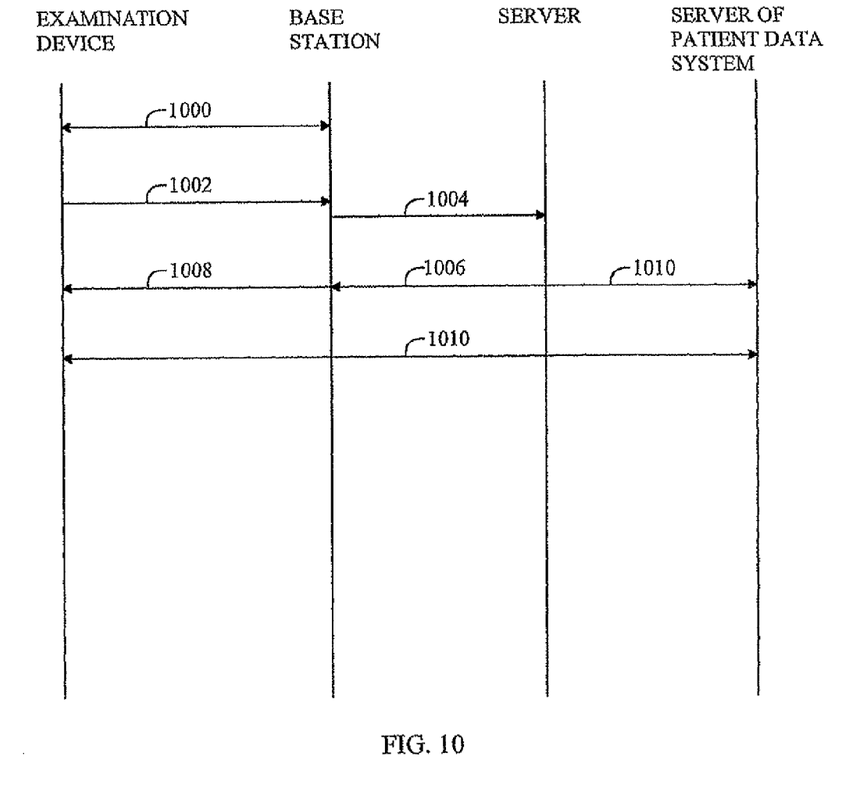
FIG. 10 shows a protocol diagram of servers.

FIG. 10 shows a protocol diagram, by which the signalling between different parts is performed. The examination device 302 may communicate in step 1000 with a wireless base station 200 of the environment in order to establish an automatic connection to the server 202 of the patient data system. The communication method of the organization and the used communication system are not yet necessarily known at this stage. Messages obtained during the communication may be stored in the examination device 302 and transmitted in step 1002 via the next wired connection or a known wireless connection to the outside of the closed network (e.g. to a consultation portal of the Internet) of the institution or to the auxiliary server 216 in the organization's network to provide a correct protocol mode with the server 202 of the patient data system via the base station 200, for example. The data of the examination device 302 may be transmitted in step 1004 to the auxiliary server 216, which returns the instruction in steps 1006 and 1008 to the examination device 302 to start the communication and which alternatively controls the server 202 of the patient data system to communicate with the examination device 302 in step 1010. A right type of connection in the step is thus provided between the server 202 of the patient data system and the examination device 302, and the transmission of patient lists to the examination device 302, the transmission of the imaged material to the server 202 of the patient data system etc. may thus begin.

With the presented solution, it is possible to speed up the patient's examination, since patient lists may be immediately displayed on the display of the camera unit, from which a doctor may select the patients and mark the performed imaging procedures as done. By means of the presented solution, the doctor may also be advised by means of information that is obtained directly via the server of the network, for example. The education of doctors may be facilitated and the teaching to do a right type of examination may be improved.

Although the different embodiments are described above with reference to the examples according to the attached drawings, it is obvious that the invention is not restricted to them but may be modified in various ways within the scope of the attached claims.

The invention claimed is:

1. A method of data transfer, the method comprising using an examination device for producing electrical data from an organ, the method comprising:
    transmitting an identifier of the examination device wirelessly from the examination device to a base station of the data transmission network of the patient data system;
    transmitting the identifier of the examination device from the base station to the auxiliary server;
    receiving the identifier determining the examination device by an auxiliary server, which has installation data associated with at least one accepted device identifier available;
    transmitting the installation data associated with the examination device identifier from the auxiliary server to a server of a patient data system;
    automatically installing the identifier determining the examination device on the basis of the installation data on the server of the patient data system for data transfer; and
    transferring data between the examination device and the server of the patient data system after installing the identifier.

2. The method of claim 1, further comprising controlling the operation of the detection unit by means of the docking station.

3. The method of claim 1, further comprising controlling the data transfer between the detection unit and the server of the patient data system by means of the docking station.

4. The method of claim 1, further comprising connecting the examination device comprising the detection unit and the docking station to the data transmission network of the patient data system; and transmitting the docking station identifier, which also determines the detection unit, from the docking station to the auxiliary server.

5. The method of claim 1, further comprising performing the data transfer between the examination device and the server of the patient data system according to a DICOM protocol.

6. The method of claim 1, further comprising performing the data transfer between the examination device and the server of the patient data system according to an HL7 protocol.

7. The method of claim 1, further comprising searching among a plurality of connections for a working connection to the base station by means of the examination device, and using at least one operating working when communicating with the base station.

8. The method of claim 1, further comprising establishing a MESH connection between the examination device and the base station.

9. The method of claim 1, further comprising establishing a GRID connection between the examination device and the base station.

10. The method of claim 1, further comprising establishing a peer-to-peer connection between the examination device and the base station.

11. The method of claim 1, further comprising transferring the identifier and the installation data in secured form.

12. A method of data transfer, the method comprising using an examination device for producing electrical data from an organ, the method comprising:
    searching for examination devices to be connected to the data transmission network of a patient data system by means of a base station, reading an identifier of a detected examination device at the base station;
    transmitting the identifier of the examination device from the base station to the auxiliary server via the data transmission network of the patient data system;
    receiving the identifier determining the examination device by an auxiliary server, which has installation data associated with at least one accepted device identifier available;
    transmitting the installation data associated with the examination device identifier from the auxiliary server to a server of a patient data system;
    automatically installing the identifier determining the examination device on the basis of the installation data on the server of the patient data system for data transfer; and
    transferring data between the examination device and the server of the patient data system after installing the identifier.

13. A method of data transfer, the method comprising using an examination device for producing electrical data from an organ, the method comprising:
    transmitting an identifier of a camera unit representing the examination device to a docking station;
    transmitting from the docking station of the camera unit to an auxiliary server at least one of the following: a camera unit identifier, a docking station identifier;
    receiving the identifier determining the examination device by an auxiliary server, which has installation data associated with at least one accepted device identifier available;
    transmitting the installation data associated with the examination device identifier from the auxiliary server to a server of a patient data system;
    automatically installing the identifier determining the examination device on the basis of the installation data on the server of the patient data system for data transfer; and transferring data between the examination device and the server of the patient data system after installing the identifier.

14. The method of claim 13, further comprising transmitting the detection unit identifier and/or the docking station identifier from the docking station to the auxiliary server via the data transmission network of the patient data system.

15. A system for data transfer, the system comprising an examination device for producing electrical data from an organ, a base station of a data transmission network of a patient data system and an auxiliary server, which has installation data associated with at least one accepted device identifier available;
the examination device is configured to transmit the identifier of the examination device wirelessly to the base station of the data transmission network of the patient data system;
the base station is configured to transmit the identifier of the examination device to the auxiliary server;
the auxiliary server being configured to receive an identifier determining the examination device and transmit the installation data associated with the examination device identifier from the auxiliary server to a server of a patient data system for an automatic installation; and
the examination device being configured to transfer data with the server of the patient data system after the identifier has been installed.

16. The system of claim 15, wherein the examination device is configured to transmit the identifier of the examination device to the auxiliary server when the examination device is connected to a data transmission network of the patient data system.

17. The system of claim 15, wherein the examination device comprises a detection unit and a docking station;
the examination device is configured to transmit the identifier of the detection unit representing the examination device to the docking station; and the docking station is configured to transmit from the docking station to the auxiliary server at least one of the following: a detection unit identifier, a docking station identifier.

18. The system of claim 17, wherein the docking station is configured to transmit the detection unit identifier and/or the docking station identifier from the docking station to the auxiliary server via the data transmission network of the patient data system.

19. The system of claim 17, wherein the docking station is configured to control the operation of the detection unit.

20. The system of claim 17, wherein the docking station is configured to control the data transfer between the detection unit and the server of the patient data system.

21. The system of claim 15, wherein the docking station is configured to transmit the docking station identifier, which also determines the detection unit, to the auxiliary server.

22. The system of claim 15, wherein the system is configured to perform the data transfer between the examination device and the server of the patient data system according to a DICOM protocol.

23. The system of claim 15, wherein the system is configured to perform the data transfer between the examination device and the server of the patient data system according to an HL7 protocol.

24. The system of claim 15, wherein the system is configured to transfer the identifier and the installation data in secured form.

25. A system for data transfer, the system comprising an examination device for producing electrical data from an organ, a base station of a data transmission network of a patient data system and an auxiliary server, which has installation data associated with at least one accepted device identifier available;
the base station is configured to search for examination devices connected to the data transmission network of the patient data system, read the identifier of the detected examination device and transmit the identifier of the examination device to the auxiliary server via the data transmission network of the patient data system;
the auxiliary server being configured to receive an identifier determining the examination device and transmit the installation data associated with the examination device identifier from the auxiliary server to a server of a patient data system for an automatic installation; and
the examination device being configured to transfer data with the server of the patient data system after the identifier has been installed.

26. The system of claim 25, wherein the examination device is configured to search among a plurality of connections for a working connection to the base station and use at least one working connection when communicating with the base station.

27. The system of claim 25, wherein the system is configured to establish a MESH connection between the examination device and the base station.

28. The system of claim 25, wherein the system is configured to establish a GRID connection between the examination device and the base station.

29. The system of claim 25, wherein the system is configured to establish a peer-to-peer connection between the examination device and the base station.

* * * * *